United States Patent
Wankhade et al.

(10) Patent No.: US 10,376,456 B2
(45) Date of Patent: Aug. 13, 2019

(54) CONCENTRATED AND SELF-PRESERVING COMPOSITIONS OF MILD SURFACTANTS FOR TRANSPARENT AND SKIN-PH PERSONAL CARE FORMULATIONS

(71) Applicant: GALAXY SURFACTANTS LTD., Navi Mumbai (IN)

(72) Inventors: Arpit Wankhade, Amravati (IN); Bhagyesh Jagannath Sawant, Kalyan (IN); Pritesh Mhatre, Raigad (IN); Nirmal Koshti, Piscataway, NJ (US); Pooja Vaidya Kshirsagar, Nagpur (IN); Ashwini Ballal, Navi Mumbai (IN); Anuradha Sharma, Navi Mumbai (IN); Kumar Raunak, Kamothe (IN)

(73) Assignee: GALAXY SURFACTANT, Navi Mumabi (IN)

( * ) Notice: Subject to any disclaimer, the term of this patent is extended or adjusted under 35 U.S.C. 154(b) by 137 days.

(21) Appl. No.: 15/559,379

(22) PCT Filed: Aug. 3, 2015

(86) PCT No.: PCT/IN2015/000309
§ 371 (c)(1),
(2) Date: Sep. 18, 2017

(87) PCT Pub. No.: WO2016/147196
PCT Pub. Date: Sep. 22, 2016

(65) Prior Publication Data
US 2019/0167554 A1    Jun. 6, 2019

(30) Foreign Application Priority Data
Mar. 16, 2015    (IN) .......................... 865/MUM/2015

(51) Int. Cl.
| | | |
|---|---|---|
| A61K 8/00 | (2006.01) |
| A61K 8/58 | (2006.01) |
| A61Q 19/10 | (2006.01) |
| A61K 8/46 | (2006.01) |
| A61K 8/42 | (2006.01) |
| A61Q 5/02 | (2006.01) |

(52) U.S. Cl.
CPC .................. *A61K 8/58* (2013.01); *A61K 8/42* (2013.01); *A61K 8/466* (2013.01); *A61Q 5/02* (2013.01); *A61Q 19/10* (2013.01); *A61K 2800/5922* (2013.01)

(58) Field of Classification Search
None
See application file for complete search history.

(56) References Cited

U.S. PATENT DOCUMENTS

| | | |
|---|---|---|
| 5,300,665 A | 4/1994 | Tracy |
| 5,490,955 A | 2/1996 | Hagan et al. |
| 8,105,994 B2 | 1/2012 | Tsaur |
| 8,114,824 B1 | 2/2012 | Dasgupta |
| 8,268,767 B2 | 9/2012 | Tsaur |

FOREIGN PATENT DOCUMENTS

| | | |
|---|---|---|
| IN | 2715 MUM 2014 | 8/2014 |
| WO | 2011/129679 | 10/2011 |
| WO | 2014/030038 A1 | 2/2014 |
| WO | WO 2014/181342 | 11/2014 |

OTHER PUBLICATIONS

Imokawa, "Exogenous Dermatology", Surfactant-Induced Depletion of Ceramides and Other Intercellular Lipids: Implication for the Mechanism Leading to Dehydration of the Stratum corneum.
Hart et al., "The lathering potential of surfactants—a simplified approach to measurement", Journal of the Society of Cosmetic Chemists, vol. 31, No. 5, 223-236.
Kastner, et al., "Hautirritationen verschiedener anionaktiver Tenside im Duhring-Kammer—Test am Menschen im Vergleich zu in vitro— und tierexperimentellen Methoden", Fette, Siefen, Anstrichmittel, vol. 83, Issue 1, pp. 33-46, 1981.
Kawai, et al., "The induction of skin tightness by surfactants", Journal of the Society of Cosmetic Chemists, vol. 35, No. 3, 147-156.
Pape, et al., "Standardization of an in vitro red blood cell test for evaluating the acute cytotoxic potential of tensides", Arzneimittel-Forschung [Apr. 1, 1990, 40(4): 498-502].
Pape, et al., "Validation of the red blood cell test system as in vitro assay for the rapid screening of irritation potential of surfactants", Mol. Toxicol. 1987-1988 Fall; 1(4): 525-36.
Ananthapadmanabhan, et al., "A Novel Technology in Mild and Moisturizing Cleansing Liquids", Cosmetic Dermatology, vol. 22, No. 6, Jun. 2006, pp. 307-316.
Ananthapadmanabhan, et al., "Cleansing without compromise: the impact of cleansers on the skin barrier and the technology of mild cleansing", Dermatologic Therapy, vol. 17, 2004, 16-26.

(Continued)

*Primary Examiner* — Necholus Ogden, Jr.
(74) *Attorney, Agent, or Firm* — Kramer Amado, P.C.

(57) ABSTRACT

The invention relates to aqueous, high active, self-preserving composition of mild surfactants which are used to create transparent liquid formulations with pH similar to skin's pH. More specifically, the composition comprise of sodium/potassium acyl isethionate of Formula I and mono potassium acyl glutamate of Formula II with solids content of at least 45 w/w, for personal care formulation that are ultra-mild, with skin pH and transparent.

8 Claims, 5 Drawing Sheets

(56) References Cited

OTHER PUBLICATIONS

Dominguez, et al., "The inhibitory effect of some amphoteric surfactants on the irritation potential of alkylsulphates", International Journal of Cosmetic Science, 3, 57-68 (1981).
Faucher, et al., "Interaction of keratinous substrates with sodium lauryl sulfate . . . I. sorption", J. of the Society of Cosmetic Chemists, vol. 29 pp. 323-337 (May 1978).
Prosperio, et al., "Nonpreservative substances able to inhibit microbial growth in cosmetics", Cosmetics & Toiletries, Edizione Italiana (1996) 17(3), 11-13, 16-19.

(Initial GLI Foam)

(GLI Foam After 5 Min.)

(Initial GI Foam)

(GI Foam After 5 Min.)

CONCENTRATED AND SELF-PRESERVING COMPOSITIONS OF MILD SURFACTANTS FOR TRANSPARENT AND SKIN-PH PERSONAL CARE FORMULATIONS

FIELD OF INVENTION

The invention relates to high active surfactant compositions of O-acyl isethionate and N-acyl glutamate for personal care. These self-preserving compositions of mild surfactants are useful to create cleansing formulations for normal skin as well as for sensitive, inflamed and diseased skin. These high active surfactant compositions of mild surfactants are suitable to make transparent personal care cleansing formulations with pH similar to that of skin's pH.

BACKGROUND AND PRIOR ART

In last few years, the understanding of the science of personal cleansing (skin and hair) has seen good advances. Skin, the largest organ in human body, is made up of two layers, dermis and epidermis. Epidermis is the outer layer and it is made up of several layers that have viable cells in different stages of differentiation. The viable keratinocytes of inner layers differentiate to non-nucleated, dead corneocytes to form the uppermost layer of epidermis called the stratum corneum (SC). The stratum corneum regulates the loss of water from human body and also protects the insides of human body from the external ravages. The stratum corneum is best described by the 'brick and mortar' model where the dead corneocytes are the bricks and the lipid bilayers are the mortar that forms the continuous domain. Both, human skin and hair gather dirt and microbes from the environment along with its own secretions of sebum. The centuries-old cleansers, like traditional soaps with very highly alkaline pH, not only swell the proteins of corneocytes but they do remove both proteins and lipids and disturb stratum corneum's function of controlling moisture leading to dryness, after-wash tightness, erythema and irritation. Cleansers are supposed to cleanse the skin of dirt, sebum and bacteria. Cleansing process also helps the natural exfoliation and rejuvenation of skin. However, when the cleansers start stripping the skin (SC of epidermis) of its lipids, proteins and natural moisturizing factor (NMF) then the skin's (stratum corneum's) function of balancing moisture is seriously compromised. This is what precisely happens with cleansers that contain very harsh and penetrating type of surfactants like soaps (sodium salt of fatty acids) and fatty alcohol sulphates (sodium dodecyl sulphate). ("The induction of skin tightness by surfactants"; M. Kawai and G. Imokawa; *J. Soc. Cosmet. Chem.* 147-156, 35(1984)). Needless to say that, cleansing with harsh surfactants is a bad choice for the sensitized and diseased skin. Better understanding of biology of skin in the last decade or so, helped formulators design cleanser systems that would be gentle on the skin. This understanding helped scientists in designing the surfactant structure that would do less damage to skin while cleansing. This deeper understanding of skin biology vis-à-vis skin cleansing resulted in emergence of "mild" surfactants and the exploitation of the synergy amongst surfactants to achieve the optimal cleansing without compromising skin's natural function. The science of skin cleansing is more or less true with hair's cleansing since structurally, hair are made up of again proteins and lipids, the percentage of protein, is obviously more as compared to skin's stratum corneum.

Mild cleansing for skin needs to be understood in the context of disrupting the normal biological structure of skin. Surfactants that are used for cleansing are classified in three main categories, e.g. anionic, amphoteric and nonionic. The cleansing and foaming properties of a surfactant depend on its nature (ionic or nonionic), the size of head group and subsequent aggregate (micelle) formation in solution.

The different types of surfactants have different interactions with skin's stratum corneum. Thus, three important constituents of stratum corneum that should not be disturbed during cleansing operations are a) proteins of corneocytes b) lipids of SC and c) NMF (natural moisturizing factor). For examples, ionic surfactants like anionic sodium dodecyl sulphate (SDS) or sodium lauryl ether sulphate (SLES) interact strongly with proteins of conmeocytes and cause irritation as a result of denaturation of proteins. In contrast to the above, electrically neutral zwitterionic surfactants, like cocoamidopropyl betaine (CAPB), interact far less with SC's proteins. Similarly, the non-ionic surfactants like alkyl polyglucosides have the least interaction with SC's proteins and hence they are almost non-irritants. The ionic surfactants (both anionics and cationics) are on the top of the list of substances with the irritation potential. For this reason, the anionic surfactant like SLES has been blended with zwitterionic CAPB for skin cleansing body washes. ("The inhibitory effect of some amphoteric surfactants on the irritation potential of alkyl sulphates"; Dominguez J. G., Balaguer F., Parra J. L., Palegero C. M., *Int. J. Cosmet. Soc.* 57-68, 3(2) (1981)). It is to be noted here that any surfactant, particularly soap type anionic sodium laurate with highly alkaline pH, is extremely harsh on skin since it is totally incompatible with the biological pH of stratum corneum which is acidic around 5 to 6. In addition, the high alkalinity of soap (pH of around 10 and above) swells the protein of corneocytes and often times intercalation of surfactant molecules in upper layers of SC causes further irritation ("Interaction of keratinous proteins with sodium lauryl sulphate": I. Sorption; Faucher J. A., Goddad E. D., *J. Soc. Cosmet. Chem.* 323-338 29, (1978)). Another very important interaction that needs to be taken into consideration while evaluating mildness of a surfactant on skin is that the reaction between surfactants and lipid bilayers of SC that form the continuous domain in which the corneocytes are embedded. Lipids are of complex nature and the main constituents are ceramides, cholesterol and its derivatives and fatty acids. ("Surfactants-induced depletion of ceramides and other intercellular lipids: implication for the mechanism leading to dehydration of stratum corneum"; Imokawa G. *Exogeneous Dermatology,* 81-98 3, (2004)). Some lipid components get easily removed by micellar solubilization and causing serious damage to SC's barrier function and modulation of transepidermal loss of water (TEWL) to the environment. Serious consequences are seen as a result of stripping away of SC's lipids (increase in TEWL, after-wash skin tightness, dryness, erythema, xerosis, cracking of skin and loss of visco-elastic (flexibility and extensibility) properties of healthy skin. It should be noted that some of the surfactants have 'mild interaction' with proteins of corneocytes and are rated as 'mild' on the scale of irritancy, like zwitterionic cocoamidopropyl betaine (CAPB) or non-ionic alkyl polyglycosides (APG). However, these two classes of surfactants are very good lipid solubilizers and hence damage the lipid bilayers of SC through micellar solubilization. So a good personal cleanser should foam and lather well (consumer desired in-use attributes) and should remove soil, dirt and bacteria on skin without damaging or altering (least surfactant induced damage) the three constituents of SC e.g. proteins, lipids and NMF. ("Cleansing without compromise": The impact of cleansers on the skin barrier and the technology of mild cleansing; Ananthapadmanabhan K. P., Moore D. J., Subramanyan K.; *Dermatol. Ther.* 16-26, 17 (2004)). So while selecting surfactants for skin cleansers formulators have to think about strategies to restore the hydration level as well the lipids lost during cleansing. The body wash formulation that meets the above criteria has been introduced to consumers in 2009. This formulated product was based on O-acyl isethionate (sodium cocoyl isethionate) as the mild surfactant. ("A novel technology in mild and moisturizing cleansing liquids"; K. P. Ananthapadmanabhan, L. Yang, C. Vincent, L. Tsaur et al.; *Cosmet. Dermatol.* 307-316, 22(6), (2009)). Subsequently, it has been shown that the combination of O-acyl isethionate and N-acyl amino acid surfactants is the most ideal for its mildness on the skin and good in-use attributes (A novel glycinate based body wash: clinical investigation into ultra-mildness, effective conditioning and improved consumer benefits. J. Regan, L-M Mollica, K. P. Ananthapadmanabhan, *J. Clinical and Aesthetic Dermatology*, 23-30, 6(6), (2013)).

This technology has been covered by U.S. Pat. No. 8,268,767 (2012) and U.S. Pat. No. 8,114,824 (2012) wherein the synergy of sodium cocoyl isethionate and sodium cocoyl glycinate has been exploited. The surfactant combinations comprising of O-acyl isethionates and N-acyl glycinates or N-acyl sarcosinates as main ingredients have been reported to be very good cleansing systems that are 'super mild/gentle' on skin and excellent delivery vehicles of actives (benefit agents like emollients, silicones, triglycerides and petrolatum).

K. P. Ananthapadmanabhan et al. have shown the synergy of sodium cocoyl isethionate and sodium cocoyl glycinate in getting the best of mildness and in-use performance for skin cleansers (*J. Clinical and Aesthetic Dermatology*, 23-30, 6(6), (2013)). Koshti et al. (PCT/IN2013/000494) demonstrated a novel way of getting the two classes (O-acyl isethionates and N-acyl amino acid surfactants) of mild surfactants manufactured as aqueous solutions in a pseudo one-pot process. In view of the synergy between sodium cocoyl isethionate and sodium cocoyl glycinate as demonstrated by K. P. Ananthapadmanabhan et al., this combination has been further studied by Kshirsagar et al. (Isotropic, flowable, skin-pH aqueous compositions comprising N-acyl glycinates as primary surfactants, Indian Patent application no. 2715/MUM/2014) wherein it has been demonstrated that using third surfactant it is possible to create clear, transparent formulations with pH similar to skin (pH of 5.0 to 6.0).

However, the major limitation for the formulations based on N-acyl glycinate as the primary surfactant as proposed by Kshirsagar et al. is that at skin pH which is on the acidic side, N-acyl glycinate gets converted in to N-acyl glycine which is insoluble in water. Thus, acyl glycinate's going to acyl glycine form significantly reduces its surfactant properties. The formulations where acyl glycinate is used as primary surfactant tend to become hazy since acyl glycine acts like a typical hydrophobe and achieving absolute transparency at skin-pH is not possible. In addition, when acyl glycinate goes to acyl glycine (equation 1 below), it adversely affects the foaming property. This foam depression and very quick lather drainage is observed in the presence of other surfactants, particularly, the mild acyl isethionates as well. Thus, combination of two mild surfactants, N-acyl glycinate (primary surfactant, Kshirsagar et al.) and O-acyl isethionate at acidic skin pH does not give consumer desired in-use attributes of good foam and lather. Thus, achieving transparency at skin pH and the consumer desired in-use attributes are not possible with combination of only glycinate-Isethionate wherein acyl glycinate is used as primary surfactant.

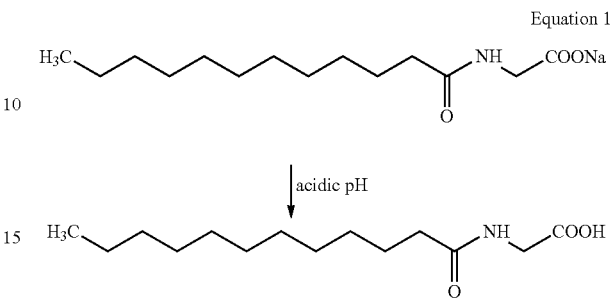

Equation 1

The inventors of the present invention surprisingly found that mild surfactant composition produced by the pseudo one pot synthesis wherein two classes of mild surfactants are produced in one pot from a single fatty raw material by reacting other reactants in sequential manner and adding lipidated glycines (Example 1) solved the problems of designing the cleansing end-formulations which have pH similar to skin's pH, mild to skin, preservative free and yet transparent.

Also due to the synergistic amplification of surfactants properties, namely foam volume and lather potential, even less amount of surfactants provides the desired performance in end formulations.

OBJECT OF THE INVENTION

It is an object of the present invention to prepare compositions of mild surfactants that would lead to synergistic performance.

It is an object of the present invention to prepare synergistic compositions of mild surfactants that would enable formulators to create transparent (clear) mild cleansing personal care formulations with excellent consumer desired in-use performance and with pH similar to skin's pH.

It is yet another object of the present invention to prepare synergistic compositions of mild surfactants that would enable formulators to create preservative-free, mild cleansing personal care formulations.

It is also an object of the present invention to prepare a mild cleansing system that would enable formulators to create personal care formulation with pH similar to the pH of skin (5 to 6), suitable for normal skin care as well as for sensitive skin with disorders like psoriasis or eczema.

It is yet another object of the present invention to prepare high active, yet easy to process compositions of mild surfactants.

SUMMARY OF THE INVENTION

The present invention relates to self-preserving, high-active, mild surfactants composition comprising:
(i) aqueous blend of O-acyl isethionates of Formula I and monopotassium N-acyl glutamate of Formula II,

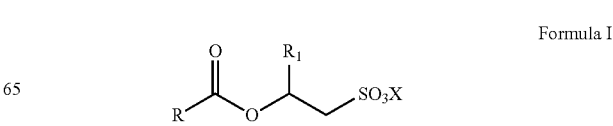

Formula I

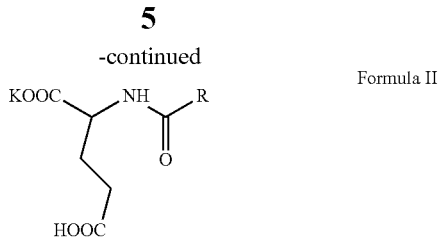

Formula II wherein, R is selected from $C_5$ to $C_{21}$ alkyl group, saturated or unsaturated, $R_1$ is selected from H or methyl, X is selected from $Na^+$ and $K^+$ and prepared by the process, comprising steps of A) reacting more than one equivalence of fatty acid chloride with alkali metal hydroxyalkyl sulphonates to prepare compounds of Formula I, B) reacting the reaction mass of step (A) (containing the remainder fatty acid chloride) with glutamic acid in the presence of potassium hydroxide under typical aqueous Schotten Baumann reaction conditions to form compounds of Formula II; wherein, the mole ratio of O-acyl isethionates of Formula I to N-acyl glutamate of Formula II is in range of 1.0:1.0 to 1.0:10.0, and (ii) 0.5 to 2% by weight mixture of N-undecylenoyl glycine and N-capryloyl glycine;

wherein, the total solids content of the composition is minimum 45% w/w and the pH of the said aqueous composition is below 6.5.

The "surfactant composition" disclosed in this invention is pseudo one-pot produced mild surfactant composition.

The term 'GLI' refers to 'O-acyl isethionate (Formula I)—N-acyl glutamate (Formula II) high active composition produced by pseudo one-pot process'.

The term 'GI' refers to 'N-acyl glycinate-O-acyl isethionate high active composition produced by pseudo one-pot process'.

The term 'preservative free' refers to 'free of preservatives mentioned in the EC directive Annex VI (1)'.

'KCGL' herein stands for 'potassium cocoyl glutamate', 'CAPB' for 'Cocoamidopropyl betaine', 'SLS' for 'sodium lauryl sulfate', 'SCG' for 'sodium cocoyl glycinate', 'SCI' for 'Sodium cocoyl isethionate', 'SLES' for 'Sodium lauryl ether sulfate', 'UG' for "Undecylenoyl glycine' and 'CG' for 'Capryloyl glycine'.

The surfactant composition of the present invention are used in personal care formulations which are desired to be mild, with skin-pH, free from preservatives and yet transparent.

BRIEF DESCRIPTION OF THE DRAWINGS

In order to better understand various exemplary embodiments, reference is made to the accompanying drawings, wherein.

DETAILED DESCRIPTION OF THE INVENTION

Figure 1:
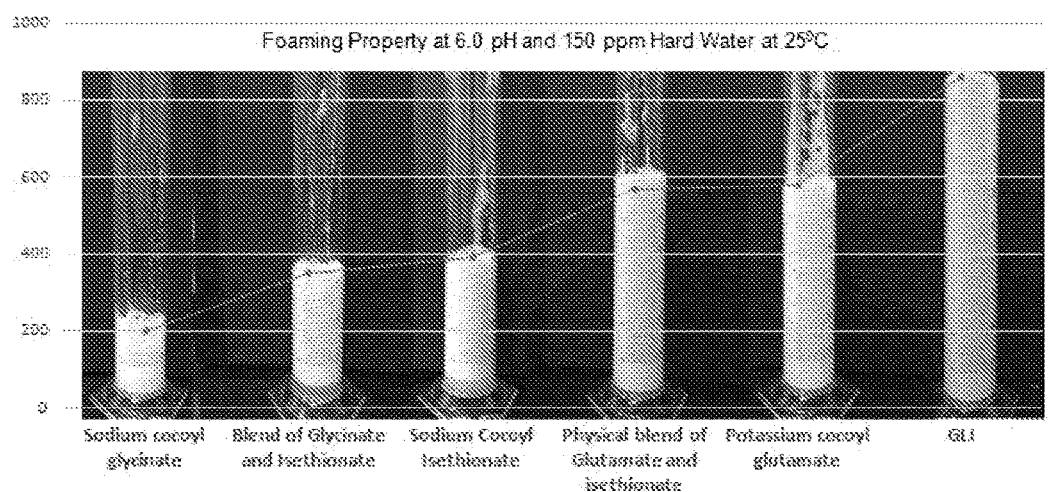
FIG. 1 shows the foaming property at pH 6.0 and 150 ppm hard water at 25° C. of various surfactant compositions, including GLI.

The present invention relates to high active, self-preserving, surfactant composition of mild surfactants. The super-mild surfactant composition of this invention is suitable to make transparent, skin-pH personal care formulations.

The present invention relates to, self-preserving, high-active, mild surfactant compositions comprising:
(i) aqueous blend of O-acyl isethionates of Formula I and monopotassium N-acyl glutamate of Formula II;

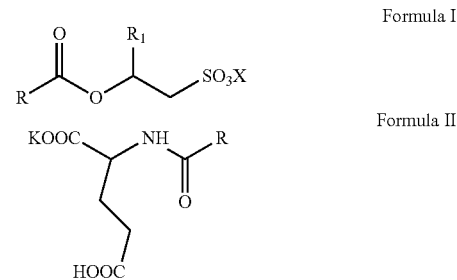

wherein, R is selected from $C_5$ to $C_{21}$ alkyl group, saturated or unsaturated, $R_1$ is selected from H or methyl, X is selected from $Na^+$ and $K^+$ and prepared by the process, comprising steps of A) reacting more than one equivalence of fatty acid chloride with alkali metal hydroxyalkyl sulphonates to prepare compounds of Formula I, B) reacting the reaction mass of step (A) (containing the remainder fatty acid chloride) with glutamic acid in the presence of potassium hydroxide under typical aqueous Schotten Baumann reaction conditions to form compounds of Formula II; wherein, the molar ratio of O-acyl isethionates of Formula I to N-acyl glutamate of Formula II is in range of 1.0:1.0 to 1.0:10.0, and (ii) 0.5 to 2% by weight mixture of N-undecylenoyl glycine and N-capryloyl glycine;

wherein, the total solids content of the composition is minimum 45% w/w and the pH of the said aqueous composition is below 6.5.

The high active, aqueous, flowable compositions of the present patent applications have been made from a common starting material, fatty acid chloride. Fatty acid chloride can be single fatty acid chloride or it can be mixture of several alkanoyl chlorides as shown in the examples (Example 1 to 5). The synthesis has been carried out wherein excess fatty acid chloride (the amount above stoichiometric excess) is reacted with dry sodium or potassium hydroxyl ethyl sulphonate to yield O-acyl isethionate of Formula-I. Gaseous hydrochloric acid generated during this reaction is then scrubbed off by absorbing it in aqueous alkali. The unreacted excess fatty acid chloride in the reaction mass is then converted into N-acyl glutamate of Formula-II in aqueous medium in the presence of potassium hydroxide under typical Schotten Baumann conditions. The amount of water used in this N-acylation is controlled to yield the desired levels of solids content (active content) of the reaction mass.

Prior to adjusting solids content of the compositions, 0.5 to 2% w/w of lipoglycines (mixture of N-capryloyl glycine and N-undecylenoyl glycine) are added (added externally or synthesized in situ) and pH adjusted to 6 to 6.5.

Ratio of N-Acyl Glutamate to N-Acyl Isethionate in GLI

The high active compositions of the present invention comprise of higher percentage of N-acyl glutamate and O-acyl isethionate. The molar ratio of O-acyl isethionates of Formula I to N-acyl glutamate of Formula II is in range of 1.0:1.0 to 1.0:10.0

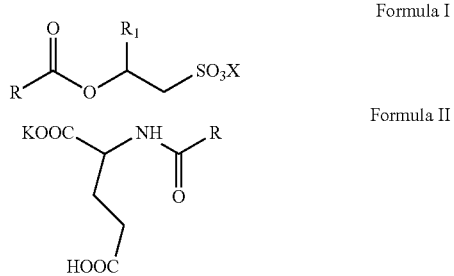

In view of in-vitro studies of property of being mild (Zein protein solubilization or protein denaturation of live blood cells) and foaming and lathering performance, it has been discovered that for the optimal performance at skin pH can be achieved with compositions wherein the isethionate to glutamate ratio varies from 1:1 to 1:10. The zein value of a blend of potassium cocoyl glutamate and sodium cocoyl isethionate is lower than that of a blend of sodium cocoyl glutamate and sodium cocoyl isethionate and hence in our invention, potassium acyl glutamate (Formula II) is preferred over its sodium salt.

Lipoglycines: N-Capryloyl Glycine and N-Undecylenoyl Glycine

The surfactant composition of the present invention contains two types of mild surfactants, namely, N-acyl amino acid surfactants and O-acyl isethionates. In addition to these two classes of mild surfactants, the compositions of the present invention also contain 0.5 to 2% w/w skin care lipoglycines, namely, N-undecylenoyl glycine (CAS No 54301-26-7) and N-capryloyl glycine (CAS No. 14246-53-8).

N-undecylenoyl glycine is known for its anti-acne and anti-dandruff properties (JP 49093521 (1974)) and commercially it is available as Lipacide UG. N-capryloyl glycine is a known derma purifier and commercially available as Lipacide C8G (Cosmetics & Toiletries, 17(3), 11-13, 16-19, (1996)). It restores skin's acidic mantle and has 5-α reductase inhibitory activity that is said to control the secretion of sebum.

In an embodiment, the lipoglycines added are 1:1 w/w mixture of N-capryloyl glycine and N-undecylenoyl glycine. These lipoglycines, N-capryloyl glycine and N-undecylenoyl glycine can be added externally after the synthesis of acyl isethionate and acyl glutamate as shown in Example 1 or they can be generated in-situ in the required amount during synthesis as demonstrated by Example 5.

Foaming and Lather Potential of Compositions of Present Invention: Synergy Between N-Acyl Glutamate and N-Acyl Isethionate Both amino acids, glycine and glutamic acid are significant part of human skin collagen (34% and 7% respectively) and human hair (6% and 11% respectively). The surfactants based on glycine and glutamic acid, N-acyl glycinate and N-acyl glutamate, have established themselves as mild to the skin. Commercially, N-acyl glycinates are available as Galsoft SCG, Hostapon SG, Gerapon CG 3S, and Amilite GCS 12K. Trade names for N-acyl glutamates are Protelan AGL 95, and Hostapon KCG.

It is reported in literature that at pH 6.5, N-acyl glutamate surfactants foam more than N-Acyl glycinate surfactants (K. Sakamoto, *Yukagaku* 44:256 (1995), *Yukagaku Journal of Japan Oil Chemists' Society*) and hence a physical blend of glutamate-isethionate is expected to foam more than a physical blend of glycinate-isethionate. The synthetic blends, GLI and GI, have been created by the process described in Example 1 and 3 respectively. GLI has been found to be significantly superior in foaming as compared to GI. The foam of GI solution at pH 6.5 collapses immediately as shown in Table I.

Synergy between N-acyl isethionate and N-acyl glycinate has been well documented by Tsaur et al., in U.S. Pat. Nos. 8,105,994 and 8,268,767. However, hitherto synergy between isethionate and glutamate has not been reported. In our study, it has been found that the foam volume of individual surfactants, potassium cocoyl glutamate and sodium cocoyl isethionate is 600 ml and 380 ml respectively, whereas for the physical mixture of glutamate and isethionate (2:1) it is 580 mL. The exceptional synergy is seen between the surfactants of the present invention (Table 1) as is evident from the superlative foaming and lathering behavior of GLI (Example 1) (foam volume 900 mL) in comparison to the physical blend of glutamate and isethionate (Example 6).

TABLE 1

Comparison of Foam volume and Lather Potential

| Surfactant (1%) at 25° C. and at pH 6.5 | Foam volume (mL) | Lather Potential (Drainage Time) |
|---|---|---|
| Potassium Cocoyl glutamate | 600 | Above 5 minutes |
| Sodium Cocoyl glycinate | 200 | Foam collapses immediately |
| Sodium Cocoyl isethionate | 380 | Foam collapses immediately |
| Sodium Cocoyl glycinate and Sodium Cocoyl isethionate (2:1) GI of Example 3 | 320 | Foam collapses immediately |
| Potassium Cocoyl glutamate and Sodium Cocoyl isethionate (2:1): physical mixing | 580 | Above 5 minutes |
| Potassium Cocoyl glutamate and Sodium Cocoyl isethionate (2:1) (GLI of | 900 | Above 5 minutes |

Physical blend is prepared by mixing the two separate surfactants, N-acyl amino acid and O-acyl isethionate (which is in solid form) and gently stirring the mixture at 70-75° C. till it becomes homogeneous. From foam height measurement, it can be easily seen that synthetically made Glutamate-Isethionate blend (GLI) is far superior to the blend of same surfactants that have been physically mixed (Example 6) (FIG. 1). Physically mixed composition of potassium cocoyl glutamate and sodium cocoyl isethionate of Example 6 develops haziness and part of it separates out on standing at room temperature. The surprisingly significant difference between GLI compositions of Example 1 and physically blended composition of Example 6 (Foam 900 cc vs Foam of 580 cc, FIG. 1 and Table 1) gets reflected in the formulation made from these surfactant systems. The compositions of Example 1 and 6 are blended with zwitterionic mild surfactant, cocoamidopropyl betaine (CAPB) and a rheology modifier Polyethylene glycol 150 distearate to get surfactant content of 12% to simulate a typical body cleansing formulations. The foam and lather drainage estimated by Hart-DeGeorge method have been found to be significantly superior for Formulation A of Example 7 than Formulation B of Example 7.

Figure 2A:
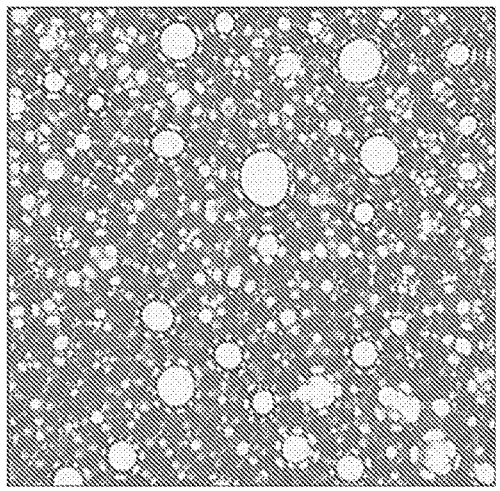
FIGS. 2A and 2B show the lather generated by GLI (initial foam in FIG. 2A; foam after 5 minutes in FIG. 2B)
Figure 2B:
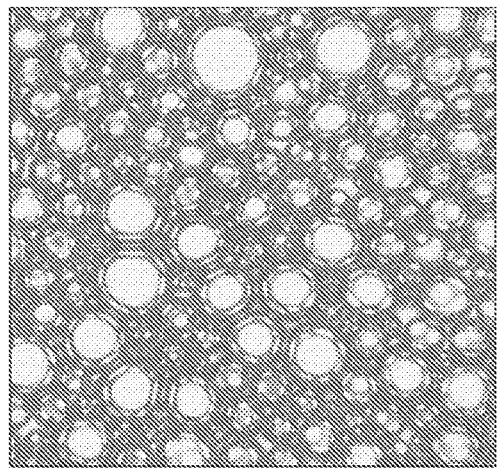
Figure 3A:
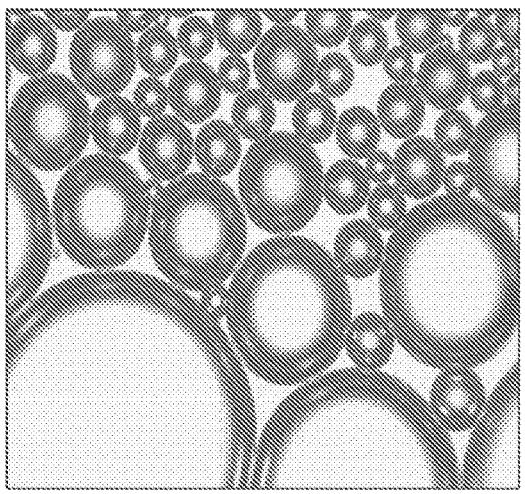
FIGS. 3A and 3B show the lather generated by GI (initial foam in FIG. 3A; foam after 5 minutes in FIG. 3B)
Figure 3B:
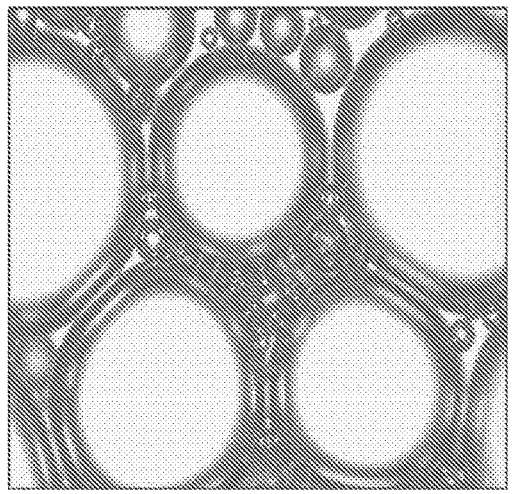

Examination of foam (1% solution at pH 6.5) under microscope also reveals that the creamy lather generated by GLI remains thick and creamy FIGS. 2A and 2B) for a long time whereas the lather of GI becomes coarser and loses its creaminess very fast (FIGS. 3A and 3B). FIGS. 2A and 2B show the initial lather generated by GLI and the lather from GLI after 5 minutes, respectively. FIGS. 3A and 3B show the initial lather generated by GI and the lather from GI after 5 minutes, respectively.

Relative Mildness of Surfactant Composition of the Present Invention

Critical Micelle Concentration (CMC) and Mildness:

It is well established that in case of surfactants, lower the CMC value, milder the surfactants. Ionic surfactant molecules interact with proteins through charge-charge interaction since the charge density on the head group is high. Whenever aggregates are formed the charge density of micelle is much lesser as the charge gets spread over the large micelle. In a solution, a surfactant that prefers to exists as micelles and not as free molecules; shows less irritancy toward skin. It can be seen from Table 2 that CMC of anionic sodium lauryl sulphate (SLS) is the highest and zwitterionic (electrically neutral) cocoamidopropyl (CAPB) is the lowest. Glutamate-Isethionate (GLI) of the present invention has the critical micelle concentration of 0.30 mM/liter exhibiting significant potential to be milder than other anionic surfactants (K. P. Ananthapadmanabhan et al., Cosmetic Dermatology, 307-316, 22(6) (2009)).

TABLE 2

| Sr. No. | Name | Molecular Weight | CMC mM/liter |
| --- | --- | --- | --- |
| 1 | CAPB | 360 | 0.06 |
| 2 | SCI | 330 | 0.14 |
| 3 | GI | 298 | 0.30 |
| 4 | GLI | 359 | 0.31 |
| 5 | SCG | 279 | 1.01 |
| 6 | KCGL | 405 | 1.01 |
| 7 | SLS | 288 | 5.90 |

Zein Protein Solubilization Assay

Mild surfactants are regarded as 'mild' because when compared with harsh surfactants, the damage done to stratum corneum by them is significantly less. The constituents of stratum corneum that get affected by surfactants are proteins (keratin of corneocytes), enzymes and lipids. Zein (corn derived protein) solubility assay is a commonly used method to predict the protein damage (proteins get denatured by surfactants) potential of surfactants [E. Gotte *Hautvertraglichkeit von Tensiden, genessen am Losevermogen fur Zein*, 4$^{th}$ *International Congress on Surfactants* 3, 83 (1064), Kastner and Forsch, *Fette, Seifen, Anshrichmittel*, 83 33-46 (1981), Lang and Spengler, Surfactants in cosmetic formulations: skin irritancy and physical properties, *Preprints of the XIVTH IFCC Congress, Barcelona*, 1, 25-37 (1986)]. Surfactant induced denaturation and solubilization of zein are associated with surfactant's skin irritation potential. For Zein protein solubilization assay, 1% solution of surfactant at pH 7.0 is used.

Figure 4:
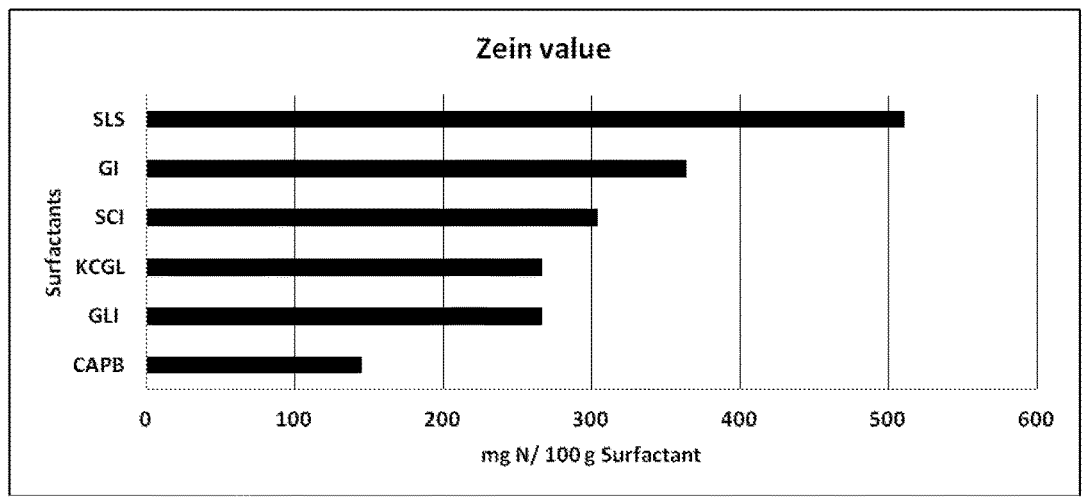
FIG. 4 shows zein values for various surfactant compositions, including GLI and GI.

Employing standard protocol for zein number determination it has been surprisingly discovered that GLI is milder than GI (FIG. 4). Zein numbers of zwitterionic cocoamidopropyl betaine (CAPB) and anionic, sodium lauryl sulphate (SLS) is mentioned to give an idea of relative mildness measurement by this in-vitro methodology.

Red Blood Cell Denaturation Index

For mildness measurement surfactant's action on human red blood cells is quantified as per the literature [W. J. W. Pape and U. Hoppe, Standardization on in-vitro red blood cell for evaluating the acute cytoxic potential of tensides, *Arzneimittel-Forschung, Publikationsorgen der Paul-Ehrlich-Gesellschaft fur Chemotherapie*, 40, 498-502 (1990), W, J. W. Pape et al., Validation of red blood cell test as an in-vitro assay for the rapid screening of irritation potential of surfactants, Molecular Toxicology, 1, 525-536 (1987)]. Surfactants solutions at 50 to 500 ppm are prepared in phosphate buffered saline and degree of haemolysis is measured on heparinized human RBCs. After the contact time of 10 minutes, the solution is centrifuged to separate RBC from the supernatant that contains oxyhaemogoblin. The absorbance is measured at 570 nm. The plot of concentration against percentage haemolysis gives the $H_{50}$.

Figure 5:
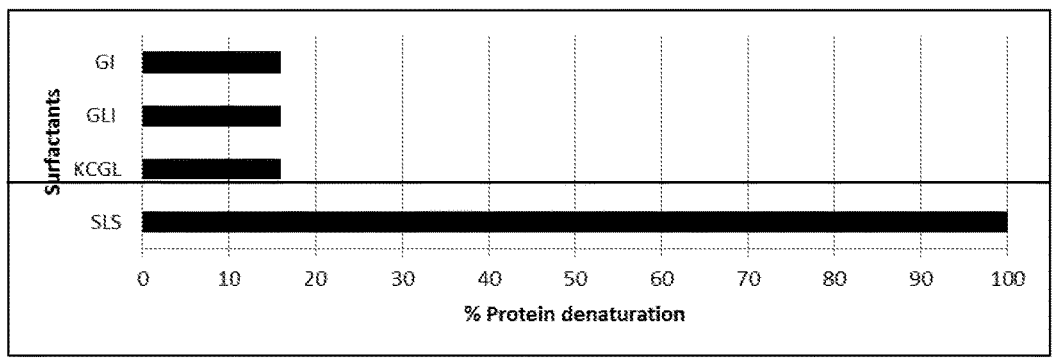
FIG. 5 shows the red blood cell denaturation index for various surfactant compositions, including GI and GLI, relative to SLS.

Taking SLS as control irritant (3.47 mmol/liter), Denaturation Index (DI) is calculated by measuring the absorbance of the supernatant that contains oxyhemoglobin after the lysis. Relative mildness of GLI and GI in comparison with standard irritant SLS is given in terms of % denaturation of proteins as given in FIG. 5. GLI has % denaturation number of 15 when SLS is considered as 100 (FIG. 5).

The ratio of $H_{50}$/DI gives the irritation potential. If the ratio is less than 1 then the surfactant is an irritant. Higher the number of L/D, lesser the potential for irritation $H_{50}$/DI ratio for GLI is found to be 5.6 and for GI it is 4.0, hence GLI is found to be milder when compared with GI.

Moisturization Efficacy of Compositions of the Present Invention

Figure 6:
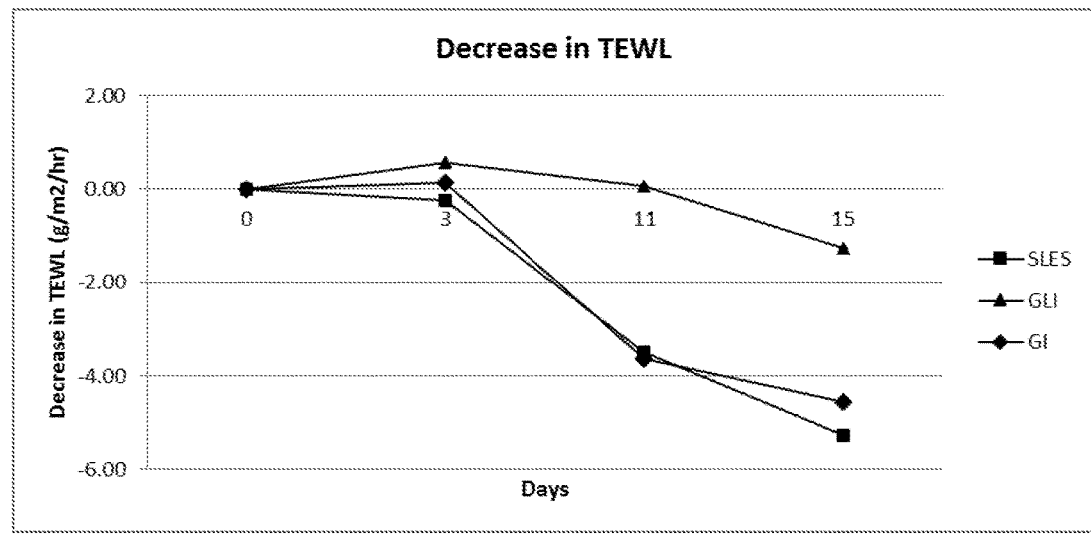
FIG. 6 shows the decrease in transepidural loss of water (TEWL) from application of various surfactants, including GI and GLI, to skin.
Figure 7:
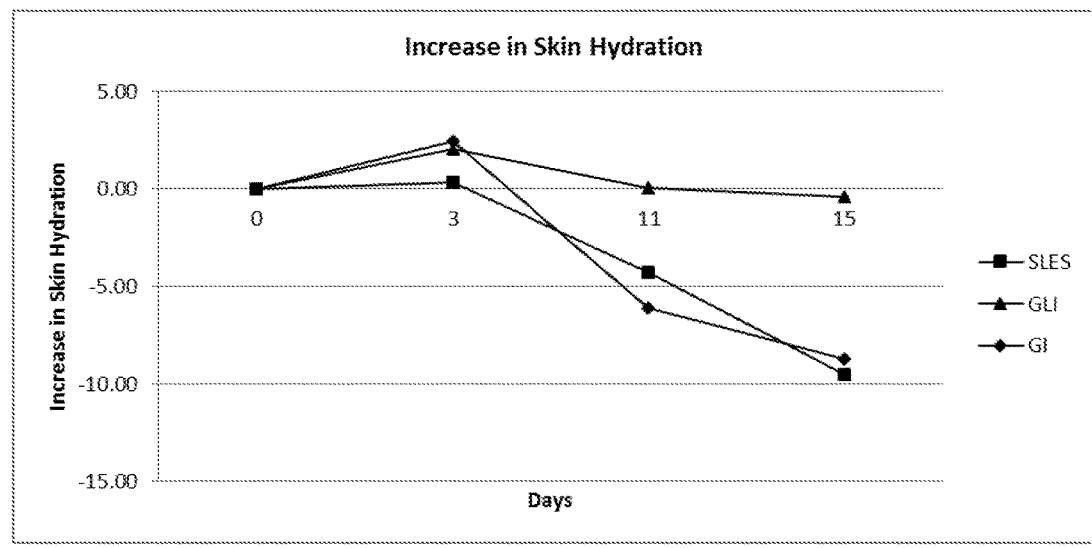
FIG. 7 shows the change in skin hydration from application of various surfactants, including GI and GLI, to skin.

GLI of Example 1 is compared with GI of Example 3. Three body-wash formulations are prepared with 12% active matter (GI, GLI and SLES (2EO) and 2% of PEG-150 distearate as viscosity builder (rheology modifier) and applied to subject's volar arm twice a day for fifteen days in a controlled relative humidity of 50% at 20° C. with acclimatization period of 30 minutes. From FIG. 6 it can be seen that on continuous application of surfactants, GLI seems to remove less amount of lipids and thus significantly less damage to stratum corneum, without altering/impacting rate of water loss. GI seems to be solubilizing lipids of SC significantly resulting in increase in TEWL. Corneometry analysis (FIG. 7) also suggests that GLI does not disturb the moisture level of skin whereas GI and sodium lauryl ether sulphate (2 EO) seem to dry the stratum corneum. Removal of Natural Moisturizing Factor (NMF) from stratum corneum during cleansing leads to a lower capacitance reading since there is less secondary bound water in the skin's corneocytes. GLI seems to remove less of NMF from stratum corneum hence does not disturb skin's hydration level. The corneometer findings are consistent with the TEWL findings.

Self-Preserving Nature of Compositions of Present Invention

Compositions of the present invention are tested for their self-preservation efficacy. The compositions contain O-acyl isethionate and N-acyl glutamate in 1:2 molar ratio. The final pH of these compositions is 6.5 and the total solids content is around 45%. The compositions have been challenge tested against Gram positive bacteria (*Staphylococcus aureus* ATCC 6538), Gram negative bacteria (*Escherichia coli* ATCC 8739, *Pseudomonas aeruginosa* ATCC 15442), yeast (*Candida albicans* ATCC 10231) and mold (*Aspergillus niger* ATCC 16404) by the usual protocol of CTFA (PCPC, Personal Care Products Council). The compositions of the present invention meet the criteria for passing the challenge test (FIG. 8).

Figure 8:
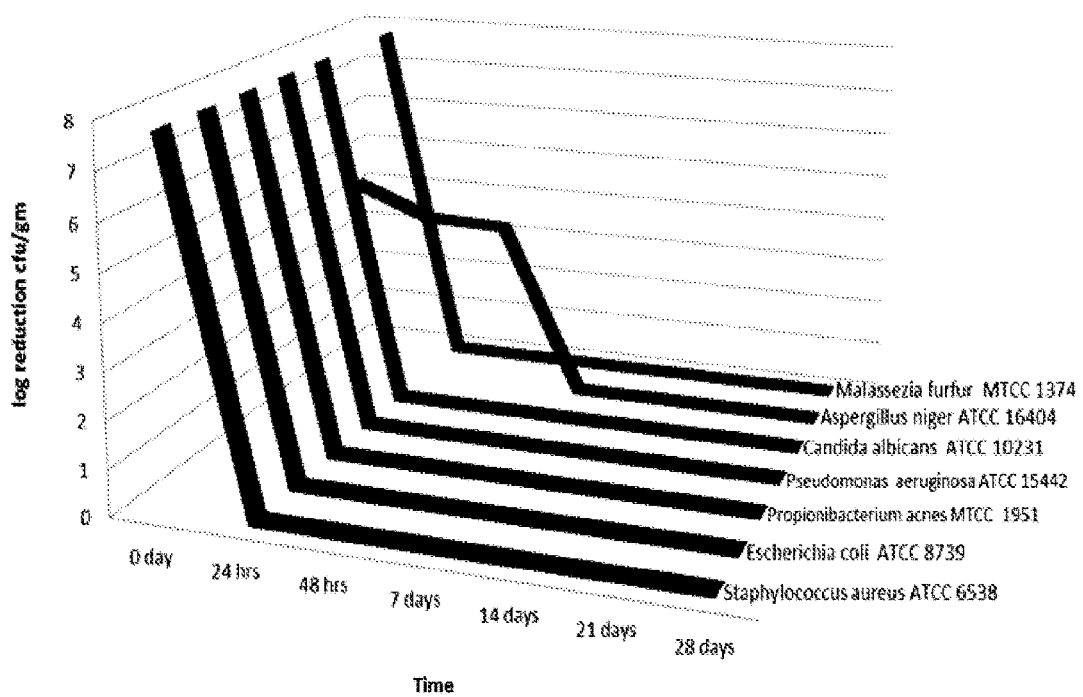
FIG. 8 shows the self-preservation efficacy of GLI compositions containing O-acyl isethionate and N-acyl glutamate in a 1:2 molar ratio.

The GLI composition of the present invention also survived when challenged with acne causing Gram positive *Propionibacterium acnes* MTCC 1951 and dandruff causing *Malassezia furfur* MTCC 1374 (FIG. 8).

Clear and Transparent Formulations with pH Similar to Skin's pH Made from Mild Surfactant Compositions of the Present Invention The compositions of the patent application allow formulators to create end-formulations that are of skin-pH and mild on skin while being transparent. The formulations detailed are 1) Body wash 2) Anti-acne face wash 3) Anti-dandruff shampoo and 4) Baby shampoo.

Using GLI of Example 1 several formulations have been prepared. A few formulations are described in the experimental section (Examples 8, 9 and 10). The characteristic common features of these formulations are transparency and pH similar to skin's pH. The transparency of the formulations has been measured with nephelometer and found to be <10 NTU, nephelometric transmittance unit (Turbidometer 2100P from HACH Company). Example 1 illustrates the making of concentrated surfactant composition of sodium cocoyl isethionate and potassium cocoyl glutamate in the molar ratio of 1:2 whereas Example 2 illustrates the synthesis of sodium lauroyl isethionate and potassium lauroyl glutamate in the same molar ratio (1:2). Example 3 illustrates synthesis of blend of sodium cocoyl isethionate and sodium cocoyl glycinate in the molar ratio of 1:2. Example 4 illustrates composition of potassium cocoyl glutamate and potassium cocoyl isethionate while Example 5 shows the in-situ synthesis of undecylenoyl glycine and capryloyl glycine in the composition of N-acyl glutamate and O-acyl isethionate.

Composition by physical blending of two surfactants, glutamate and isethionate is exemplified by Example 6. The composition made with physically blended sodium cocoyl isethionate and potassium cocoyl glutamate (45% solids, Example 6) is hazy and the turbidity is reflected in NTU unit of 30.

The surfactant composition of the present invention can optionally contain cosmetic benefit agents. Cosmetic benefit agents may be selected from polymers, humectants, rheology modifiers, anti oxidants, fragrances, emollient, conditioning agents, moisturizers, pearlisers etc.

The Advantages of Present Invention

1. The present invention teaches the synergy of the two of the well established mild surfactants, namely, mono potassium acyl glutamate and sodium or potassium acyl isethionate when they are synthesized in a particular way. The synergy between these two mild surfactants is seen on three counts, a) foaming property b) lather potential and 3) mildness toward skin. Foam and lather of synthetic GLI is far superior to physically blended mixture of acyl glutamate and acyl isethionate (Table 1) Mildness as well as foaming/lathering properties of acyl glutamate and acyl isethionate composition of the present invention is superior to recently reported acyl glycinate-acyl isethionate combinations at skin pH 5.5 to 6.5. Zein number, RBC test, CMC data and moisturization data together show that the composition of Glutamate-Isethionate (GLI) to be milder towards skin than Glycinate-Isethionate (GI) at skin pH.

2. The present invention discloses a concentrated, yet flowable aqueous compositions of mild surfactants (45 to 50% solids content), mono potassium cocoyl glutamate and sodium or potassium cocoyl isethionate. Concentrated form of the compositions of the present invention make them more eco-friendly than the other current commercial surfactants. Thousands of metric tonnes of surfactant solutions are transported across the continent every day. Saving of transportation cost and reducing carbon footprint is extremely essential and relevant for the overall sustainability.

3. The compositions of the present invention are high active, flowable, low viscous liquids providing extreme ease for creating personal care cleansing formulations (8 to 16% active mild surfactants) with pH that is similar to pH of skin.

4. Creating personal care formulations without preservatives is extremely important since all the work-horse antimicrobial preservatives are implicated in serious toxicity towards either human or to the environment. Personal care industry is trying to go away from the controversial preservatives such as parabens, methyl and chloromethyl isothiazolinone (Kathon CG), Trichlosan, formaldehyde releasers like DMDM hydantoin, Imidazolidine urea, and Iodopropynyl butyl carbamate. The compositions of the present invention allow formulators to prepare end formulations without any toxic preservatives (Examples 8 to 10). The compositions with mild surfactants and without any toxic preservatives are suitable for baby products and sensitive skin with skin conditions such as psoriasis or eczema.

EXAMPLES

The invention will now be illustrated with the help of examples. Examples illustrate the performance and the benefits through the formulations. The examples are by way of illustrations only and in no way restrict the scope of invention. Many changes and modifications can be made within the scope of the present invention without departing from the spirit thereof and the invention concluded all such modifications. A few formulations of skin and hair care preparations incorporating the compositions of the present invention are given in Examples 8 to 10.

The foam height and lather potential study was carried out by method reported in *J. Soc. Cosmet. Chem.* 223-236, 31, (1980).

Fatty acids chlorides were prepared as per the procedure reported in the Patent Application (WO2014181342) by Koshti et al. (Method to produce blends of O-acyl isethionates and N-acyl amino acid surfactants).

Example 1

Synthesis of Surfactant Composition of Sodium Cocoyl Isethionate and Mono Potassium Cocoyl Glutamate in Molar Ratio of 1:2 and 1% w/w of Lipoglycines, Undecylenoyl Glycine and Capryloyl Glycine (1:1 w/w).

The cocoyl chloride used in this experiment had the following alkyl chain distribution $C_8$: 5.0%, $C_{10}$: 6.0%, $C_{12}$:

62.6%, $C_{14}$: 20.0%, $C_{16}$: 6.0%, $C_{18}$: 0.4% To a stirred cocoyl chloride (328 g, 1.5 gmol) under slow purging of nitrogen at room temperature, sodium isethionate (74 g, 0.5 gmol) was added and the slurry was stirred at 55-60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 $cm^{-1}$), sodium cocoyl isethionate (carbonyl of ester at 1734 $cm^{-1}$) and disappearance of hydroxyl stretch (3323 $cm^{-1}$) of sodium isethionate.

This fluid viscous reaction mass (380 g) was cooled to room temperature and then added slowly to a stirred aqueous solution of L-glutamic acid (155 g, 1.05 gmol) in water (545 g) along with potassium hydroxide solution (50%, 350 g, 3.1 gmol) simultaneously while maintaining the pH of the reaction mass between 10.0 to 10.5 and the temperature between 20 to 30° C. The addition was completed in two hours and the reaction mass was stirred for another 4 h at rt. To this mixture N-capryloyl glycine (7 g) and N-undecylenoyl glycine (7 g) were added and stirred until homogeneous. The pH was adjusted to 6.0 with HCl. The solids content of the reaction mass was adjusted to 45% solids content to yield 1430 g of aqueous solution as final product.

The analysis of the above aqueous surfactant blend was as follows:

| Test | Results |
|---|---|
| Appearance | Light yellow clear liquid |
| Viscosity at 25° C. | 400 cps |
| pH as such | 6.2 |
| KCl, % w/w | 6.25 |
| Total solids, % w/w | 45.00 |
| Free glutamic acid % w/w | 2.30 |
| Free fatty acid % w/w | 3.55 |

Example 2

Synthesis of a Composition of Sodium Lauroyl Isethionate and Mono Potassium Lauroyl Glutamate in Molar Ratio of 1:2 and 1% w/w of Lipoglycines, Undecylenoyl Glycine and Capryloyl Glycine (1:1 w/w).

To a stirred lauroyl chloride (218.5 g, 1.0 gmol) under slow purging of nitrogen at room temperature, sodium isethionate (49.5 g, 0.333 gmol) was added and the slurry was stirred at 65-70° C. for 4 h. The HCl gas generated was absorbed in alkali solution and the progress of reaction was monitored by IR spectrum analysis. The FTIR spectrum of the intermediate showed the presence of unreacted lauroyl chloride (carbonyl stretch at 1800 $cm^{-1}$), sodium lauroyl isethionate (carbonyl of ester at 1734 $cm^{-1}$) and disappearance of hydroxyl stretch (3323 $cm^{-1}$) of sodium isethionate.

This fluid viscous reaction mass (255 g) was cooled to room temperature and then added slowly to a stirred aqueous solution of L-glutamic acid (103 g, 0.7 gmol) in water (296 g) along with potassium hydroxide solution (50%, 232 g, 2.066 gmol) simultaneously while maintaining the pH of the reaction mass between 10.0 to 10.5 and the temperature between 20 to 30° C. The addition was completed in two hours and the reaction mass was stirred for another 4 h at rt. To this mixture N-capryloyl glycine (4.5 g) and N-undecylenoyl glycine (4.5 g) were added and stirred until homogeneous. The pH was adjusted to 6.0 with HCl. The solids content of the reaction mass was adjusted to 50% to yield 886 g of aqueous thin paste as the final product.

The analysis of the above aqueous surfactant blend was as follows:

| Test | Results |
|---|---|
| Appearance | White flowable paste |
| Viscosity at 25° C. | 1600 cps |
| pH as such | 6.45 |
| KCl, % w/w | 6.90 |
| Total solids, % w/w | 50.00 |
| Free glutamic acid % w/w | 2.30 |
| Free fatty acid % w/w | 3.0 |

Example 3

Synthesis of a Composition of Sodium Cocoyl Isethionate and Sodium Cocoyl Glycinate in Molar Ratio of 1:2 and 1% w/w of Lipoglycines, Undecylenoyl Glycine and Capryloyl Glycine (1:1 w/w).

The cocoyl chloride used in this experiment had the following alkyl chain distribution $C_8$: 5.0%, $C_m$: 6.0% $C_{12}$: 62.6% $C_{14}$: 20.0% $C_{16}$: 6.0% $C_{18}$: 0.4% To a stirred cocoyl chloride (234 g, 1.05 gmol) under slow purging of nitrogen at room temperature, sodium isethionate (52 g, 0.35 gmol) was added and the slurry was stirred at 55-60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 $cm^{-1}$), sodium cocoyl isethionate (carbonyl of ester at 1734 $cm^{-1}$) and disappearance of hydroxyl stretch (3323 $cm^{-1}$) of sodium isethionate.

This fluid viscous reaction mass (270 g) was cooled to room temperature and then added slowly to a stirred aqueous solution of glycine (53.55 g, 0.71 gmol) in water (730 g) along with sodium hydroxide solution (48.8%, 116 g, 1.41 gmol) simultaneously while maintaining the pH of the reaction mass between 10.2 to 10.5 and the temperature between 20 to 30° C. The addition was completed in two hours and the reaction mass was stirred for another 4 h at 25° C. To this mixture N-capryloyl glycine (6.0 g) and N-undecylenoyl glycine (6.0 g) were added and stirred until homogeneous. The pH was adjusted to 7.5 with HCl. The solids content of the reaction mass was adjusted to 30% to yield 1169 g of aqueous solution as final product.

The analysis of the above aqueous surfactant blend was as follows:

| Test | Results |
|---|---|
| Appearance | Light yellow clear liquid |
| Viscosity at 25° C. | 400 cps |
| pH as such | 7.5 |
| NaCl, % w/w | 3.7 |
| Free glycine | 0.75 |
| Free fatty acid | 2.4 |
| Total solids, % w/w | 31.00 |

Example 4

Synthesis of a Composition of Potassium Cocoyl Isethionate and Mono Potassium Cocoyl Glutamate in Molar Ratio of 1:2 and 1% w/w of Lipoglycines, Undecylenoyl Glycine and Capryloyl Glycine (1:1 w/w).

The cocoyl chloride used in this experiment had the following alkyl chain distribution $C_8$: 5.0%, $C_m$: 6.0%, $C_{12}$:

62.6%, $C_{14}$: 20.0%, $C_{16}$: 6.0%, $C_{18}$: 0.4% To a stirred cocoyl chloride (328 g, 1.5 gmol) under slow purging of nitrogen at room temperature, potassium isethionate (82 g, 0.5 gmol) was added and the slurry was stirred at 55–60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 $cm^{-1}$), potassium cocoyl isethionate (carbonyl of ester at 1734 $cm^{-1}$) and disappearance of hydroxyl stretch (3323 $cm^{-1}$) of potassium isethionate.

This fluid viscous reaction mass (388 g) was cooled to room temperature and then added slowly to a stirred aqueous solution of L-glutamic acid (155 g, 1.05 gmol) in water (600 g) along with potassium hydroxide solution (50%, 350 g, 3.1 gmol) simultaneously while maintaining the pH of the reaction mass between 10.0 to 10.5 and the temperature between 20 to 30° C. The addition was completed in two hours and the reaction mass was stirred for another 4 h at rt. To this mixture N-capryloyl glycine (7 g) and N-undecyleynoyl glycine (7 g) were added and stirred until homogeneous. The pH was adjusted to 6.0 with HCl. The solids content of the reaction mass was adjusted to 45% solids content to yield 1505 g of aqueous solution as final product.

The analysis of the above aqueous surfactant blend was as follows:

| Test | Results |
|---|---|
| Appearance | Light yellow clear liquid |
| Viscosity at 25° C. | 400 cps |
| pH as such | 6.2 |
| KCl, % w/w | 6.4 |
| Total solids, % w/w | 45.00 |
| Free glutamic acid % w/w | 2.40 |
| Free fatty acid % w/w | 3.60 |

Example 5

Synthesis of a Composition of Sodium Cocoyl Isethionate and Mono Potassium Cocoyl Glutamate in Molar Ratio of 1:2 and 2% w/w of Lipoglycines, Undecylenoyl Glycine and Capryloyl Glycine (1:1 w/w). (In-Situ Generation of UG/CG)

The cocoyl chloride used in this experiment had the following alkyl chain distribution $C_8$: 5.0%, $C_{12}$: 62.0%, $C_{14}$: 18.0%, $C_{16}$: 6.0%, $C_{18}$ (oleic): 4.0% To a stirred cocoyl chloride (331 g, 1.5 gmol) under slow purging of nitrogen at room temperature, sodium isethionate (74 g, 0.5 gmol) was added and the slurry was stirred at 55-60° C. for 4 h. The HCl gas generated was absorbed in alkali solution and the progress of reaction was monitored by IR spectrum analysis. The FTIR spectrum of the intermediate showed the presence of unreacted cocoyl chloride (carbonyl stretch at 1800 $cm^{-1}$), sodium cocoyl isethionate (carbonyl of ester at 1734 $cm^{-1}$) and disappearance of hydroxyl stretch (3323 $cm^{-1}$) of sodium isethionate.

This fluid viscous reaction mass (385 g) was cooled to room temperature and then added slowly to a stirred aqueous solution of L-glutamic acid (155 g, 1.05 gmol) in water (600 g) along with potassium hydroxide solution (350%, g, 3.1 gmol) simultaneously while maintaining the pH of the reaction mass between 10.0 to 10.5 and the temperature between 20 to 30° C. To this mixture glycine (10.3 g, 0.137 gmol) was added and stirring continued. To this stirred mass mixture of undecylenoyl chloride and capryloyl chloride (25 g, 0.137 gmol) were added and the pH was maintained between 10.0 to 10.5. The reaction mass was then stirred for additional 4 hours and the pH was adjusted to 6.0 with HCl. The solids content of the reaction mass was adjusted to 45% solids content to yield 1600 g of aqueous solution as final product.

The analysis of the above aqueous surfactant blend was as follows:

| Test | Results |
|---|---|
| Appearance | Light yellow clear liquid |
| Viscosity at 25° C. | 400 cps |
| pH as such | 6.0 |
| KCl, % w/w | 6.7 |
| Total solids, % w/w | 45.00 |
| Free glutamic acid % w/w | 2.30 |
| Free fatty acid % w/w | 3.55 |

Example 6

Comparative Example

Composition of Sodium Cocoyl Isethionate and Potassium Cocoyl Glutamate, Made by Physical Blending of the Same in Molar Ratio of 1:2 and 1% w/w of Lipoglycines, Undecylenoyl Glycine and Capryloyl Glycine (1:1 w/w).

To a stirred mixture of monopotassium cocoyl glutamate (825 g, 48% solids solution) and water (250 ml) at 70° C., sodium cocoyl isethionate (155 g) is added and stirring is continued till a homogeneous solution is formed. The solid content is adjusted to 44.5%. The solution appears uniform but is hazy to naked eye. Turbidity on nephelometer is found to be 30 NTU. However, on standing sodium cocoyl isethionate precipitate out/crystallize out and settles at the bottom of the container.

| Test | Results |
|---|---|
| Appearance | Light yellow hazy liquid |
| Viscosity at 25° C. | 350 cps |
| pH as such | 6.1 |
| KCl, % w/w | 7.2 |
| Total solids, % w/w | 44.50 |

Example 7: Formulations Prepared from Composition of Example 1 and Example 6

Analysis of Formulation A: Viscosity 4000 cps at 25° C., pH as it is 6.0

| Formulation A | Ingredient | % w/w |
|---|---|---|
| | GLI of Example 1 | 26.5 |
| | Cocoamidopropyl betaine | 10 |
| | PEG 150 distearate | 3 |
| | Water | q.s. to 100 |

Analysis of Formulation B: Viscosity 4000 cps at 25° C., pH as it is 6.0.

| Formulation B | Ingredient | % w/w |
|---|---|---|
| | Physical blend of Example 6 | 26.5 |
| | Cocoamidopropyl betaine | 10 |
| | PEG 150 distearate | 3 |
| | Water | q.s. to 100 |

Comparison of Foam Volume and Lather Potential

|  | Foam volume (ml) | Lather Potential (Drainage Time) (seconds) |
|---|---|---|
| Formulation A | 510 | 240 |
| Formulation B | 360 | 30 |

Example 8: Preparation of Transparent, Skin-pH Bodywash Using Composition of Example 1

| Phase | Ingredient | % w/w | Function |
|---|---|---|---|
| A | GLI (Example 1) | 20.6 | Mild surfactant |
|  | Cocoamidopropyl betaine | 16.7 | Mild surfactant |
|  | PEG 150 distearate | 2 | Rheology modifier |
|  | Water | q.s. to 100 |  |
| B | Undecylenoyl glycine | 0.5 | Scalp care |
|  | Capryloyl glycine | 0.5 | Sebum controller |
|  | EDTA disodium | 1.0 | Chelating agent |
|  | Fragrance | 1.0 | Fragrance |

Analysis: Viscosity = 6000 cps, pH = 5.6 and Transparency <10 NTU

Example 9: Preparation of Transparent Anti-Acne Face-Wash Using Composition of Example 1

| Phase | Ingredient | % w/w | Function |
|---|---|---|---|
| A | GLI (Example 1) | 14.7 | Mild surfactant |
|  | Cocoamidopropyl betaine | 10 | Mild surfactant |
|  | PEG 150 distearate | 2 | Rheology modifier |
|  | Water | q.s. to 100 |  |
|  | Salicylic acid | 2.0 | Anti-acne |
| B | EDTA disodium | 0.1 | Chelating agent |
|  | Fragrance | 0.5 |  |
|  | Unecylenoyl glycine | 0.5 | Skin care agent |
|  | Capryloyl glycine | 0.5 | Skin care agent |

Analysis: Viscosity = 1500 cps, pH = 4 and Transparency <10 NTU

Example 10: Preparation of Transparent, "Sulphate-Free" "Anti-Dandruff" Shampoo Using Composition of Example 1

| Phase | Ingredient | % w/w | Function |
|---|---|---|---|
| A | GLI (Example 1) | 24 | Mild surfactant |
|  | Cocoamidopropyl betaine | 20 | Mild surfactant |
|  | PEG 150 distearate | 2 | Rheology modifier |
|  | Water | q.s. to 100 |  |
| B | Ketoconazole | 1.0 | Anti-dandruff agent |
|  | EDTA disodium | 0.1 | Chelating agent |
|  | Fragrance | 0.5 |  |
|  | Unecylenoyl glycine | 0.5 | Skin care agent |
|  | Capryloyl glycine | 0.5 | Skin care agent |

Analysis: Viscosity = 1000 cps, pH = 7 and Transparency <10 NTU

Example 11: Preparation of Transparent, Baby Shampoo Using Composition of Example 1

| Phase | Ingredient | % w/w | Function |
|---|---|---|---|
| A | GLI (Example 1) | 11.8 | Mild surfactant |
|  | Cocoamidopropyl betaine | 13.4 | Mild surfactant |
|  | Lauryl Glucoside | 8 | Rheology modifier |
|  | Water | q.s. to 100 |  |
|  | Polyquaternium 10 | 0.4 | Conditioning agent |
| B | Undecylenoyl glycine | 0.5 | Skin care agent |
|  | Capryloyl glycine | 0.5 | Skin care agent |
|  | EDTA disodium | 0.1 | Chelating agent |

Analysis: Viscosity = 9000 cps, pH = 5.2 and Transparency <10 NTU

We claim:

1. A mild surfactant composition comprising;
(i) aqueous blend of O-acyl isethionates of Formula I and monopotassium N-acyl glutamate of Formula II;

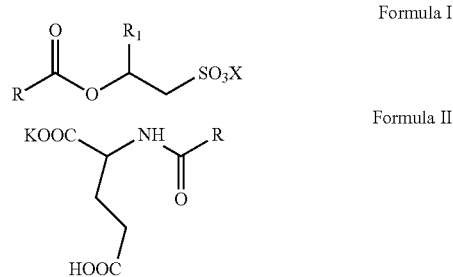

wherein, R is selected from $C_5$ to $C_{21}$ alkyl group, saturated or unsaturated, $R_1$ is selected from H or methyl, X is selected from $Na^+$ or $K^+$ and prepared by the process, comprising steps of
A) reacting more than one equivalence of fatty acid chloride with alkali metal hydroxyalkyl sulphonates to prepare compounds of Formula I,
B) reacting the reaction mass of step (A) (containing the remainder fatty acid chloride) with glutamic acid in the presence of a potassium hydroxide under typical aqueous Schotten Baumann reaction conditions to form compounds of Formula II; wherein, the molar ratio of O-acyl isethionates of Formula I to N-acyl glutamate of Formula II is in range of 1.0:1.0 to 1.0:10.0, and
(ii) 0.5 to 2% by weight mixture of N-undecylenoyl glycine and N-capryloyl glycine;
wherein, the total solids content of the composition is at least 45% w/w and the pH of the said aqueous composition is below 6.5.

2. The surfactant composition of claim 1 wherein glutamic acid is selected from L-glutamic acid or D-glutamic acid or mixture thereof.

3. The surfactant composition as claimed in claim 1, wherein the mixture of N-undecylenoyl glycine and N-capryloyl glycine is in the ratio of 1:1.

4. The surfactant composition as claimed in claim 1, which is self-preserving.

5. The personal care formulation using the aqueous surfactant composition of claim 1.

6. The transparent, skin-pH personal care formulation using the aqueous surfactant composition of claim 1.

7. The personal care formulation as claimed in claim 5 is selected from shampoo, hand wash, body wash, face wash, shower gel, and baby bubble bath.

8. The surfactant composition as claimed in claim 1 containing other cosmetic benefit agents.

* * * * *